United States Patent [19]

Eilingsfeld et al.

[11] 4,153,607

[45] May 8, 1979

[54] PROCESS FOR THE PRODUCTION OF 4,5-DISUBSTITUTED THIAZOLES

[75] Inventors: Heinz Eilingsfeld, Frankenthal; Guenther Seybold, Ludwigshafen, both of Fed. Rep. of Germany

[73] Assignee: BASF Aktiengesellschaft, Fed. Rep. of Germany

[21] Appl. No.: 880,883

[22] Filed: Feb. 24, 1978

[30] Foreign Application Priority Data

Mar. 28, 1977 [DE] Fed. Rep. of Germany ....... 2713573

[51] Int. Cl.$^2$ .......................................... C07D 417/02
[52] U.S. Cl. .............................. 260/306.8 F; 260/158
[58] Field of Search ................................. 260/306.8 F

[56] References Cited

U.S. PATENT DOCUMENTS

| | | | |
|---|---|---|---|
| 3,726,891 | 4/1973 | Pilgram et al. | 260/306.8 F |
| 3,878,222 | 4/1975 | Spicer et al. | 260/306.8 F |
| 4,009,164 | 2/1977 | Beard | 260/306.8 F |

*Primary Examiner*—Nicholas S. Rizzo
*Attorney, Agent, or Firm*—Keil & Witherspoon

[57] ABSTRACT

4,5-Disubstituted thiazoles are manufactured by reacting 4-amino-5-cyano-thiazoles with hydrogen sulfide in the presence of basic compounds, followed by dehydrogenating cyclization. The new 3-amino-thiazolo-(4,5-c)-isothiazoles I, 4-amino-5-thiocarbamidothiazoles III and 4,5-disubstituted thiazoles IV obtainable by the process of the invention are valuable intermediates for the manufacture of azo dyes and of crop protection agents.

12 Claims, No Drawings

PROCESS FOR THE PRODUCTION OF 4,5-DISUBSTITUTED THIAZOLES

The present invention relates to 4,5-disubstituted thiazoles and to a process for their manufacture by reacting 4-amino-5-cyanothiazoles with hydrogen sulfide in the presence of a basic compound, followed by dehydrogenating cyclization.

We have found that a 3-amino-thiazole-(4,5-c)-isothiazole of the formula

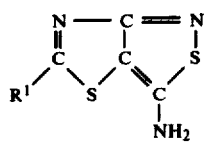
I where $R^1$ is hydrogen, an aliphatic, araliphatic or aromatic radical,

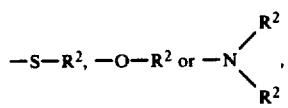

the individual radicals $R^2$ are identical or different and each is an aliphatic, araliphatic or aromatic radical and the two radicals $R^2$ present as substituents of the nitrogen atom may also form, together with the latter, a heterocyclic radical is obtained in an advantageous manner if, in a first step, a 4-amino-5-cyano-thiazole of the formula

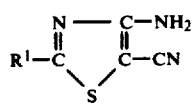
II, where $R^1$ has the above meaning, is reacted with hydrogen sulfide in the presence of a basic compound, and, in a second step, the resulting 4-amino-5-thiocarbamido-thiazole of the formula

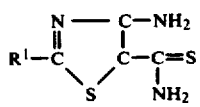
III, where $R^1$ has the above meaning, is cyclized in the presence of a dehydrogenating agent.

Further, we have found the new 4,5-disubstituted thiazoles of the formula

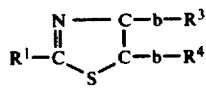
IV, where $R^1$ is hydrogen, an aliphatic, araliphatic or aromatic radical,

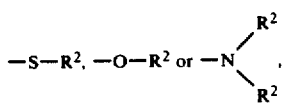

the individual radicals $R^2$ are identical or different and each is an aliphatic, araliphatic or aromatic radical and the two radicals $R^2$ present as substituents of the nitrogen atom may also form, together with the latter, a heterocyclic radical, each b is a single bond and $R^3$ is amino and $R^4$ is thiocarbamido, or $R^3$ and $R^4$ are

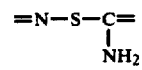

and each b is a double bond.

Further, we have found the new 3-amino-thiazole-(4,5-c)-isothiazoles of the formula

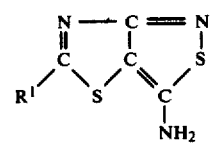
I where $R^1$ is hydrogen, an aliphatic, araliphatic or aromatic radical,

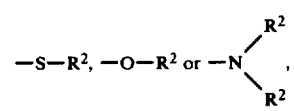

the individual radicals $R^2$ are identical or different and each is an aliphatic, araliphatic or aromatic radical and the two radicals $R^2$ present as substituents of the nitrogen atom may also form, together with the latter, a heterocyclic radical.

Further, we have found the new 4-amino-5-thiocarbamido-thiazoles of the formula

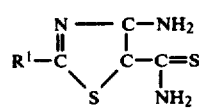
III, where $R^1$ is hydrogen, an aliphatic, araliphatic or aromatic radical,

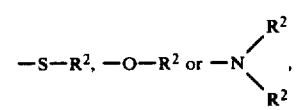

the individual radicals $R^2$ are identical or different and each is an aliphatic, araliphatic or aromatic radical and the two radicals $R^2$ present as substituents of the nitrogen atom may also form, together with the latter, a hetercyclic radical.

If 2-methylmercapto-4-amino-5-cyanothiazole is used with bromine as the dehydrogenating agent, the reaction can be represented by the following equations:

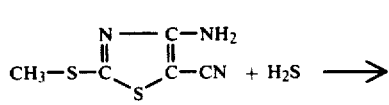

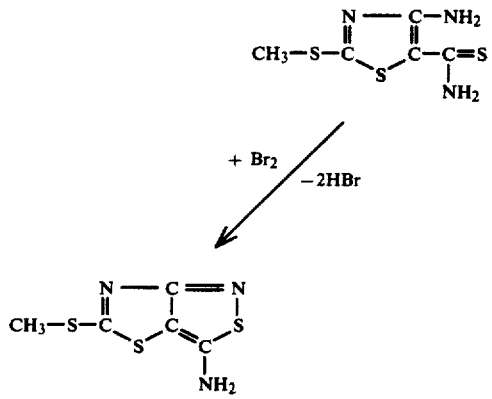

Using the process according to the invention, the new 4-amino-5-thiocarbamido-thiazoles and 3-amino-thiazolo-(4,5-c)-isothiazoles are obtained in a simple and economical manner, in good yield and high purity.

The starting materials II can be manufactured by conventional methods, for example by reacting chloroacetonitrile with N-cyanothiolimido-acid (Archiv der Pharmacie, 303 (1970), 625–633) or with the alkali metal salts of cyanoamido-dithiocarbonic acid (Annalen, 764 (1972), 125–130). Reaction of 2-mercapto-4-amino-5-cyano-thiazoles with secondary amines, advantageously in a suitable solvent, e.g. dimethylformamide, toluene, carbon tetrachloride, chlorobenzene or, especially, dimethyl sulfoxide or hexamethylphosphorotriamide, gives the corresponding 2-amino compounds in which the nitrogen in the 2-position is disubstituted.

In the first step, the starting materials II can be reacted with hydrogen sulfide in stoichiometric amount, or with either component in excess, advantageously in a ratio of from 1 to 3, preferably from 1 to 1.2, moles of hydrogen sulfide per mole of starting material II. Instead of hydrogen sulfide, compounds which form hydrogen sulfide under the reaction conditions may also be used, e.g. ammonium sulfide or alkali metal sulfides, especially sodium sulfide, potassium sulfide, ammonium bisulfide or alkali metal bisulfide, especially sodium bisulfide and potassium bisulfide. Preferred starting materials II and, accordingly, preferred compounds III, IV and I are those where $R^1$ is hydrogen, alkyl of 1 to 6 carbon atoms, aralkyl of 7 to 12 carbon atoms, phenyl,

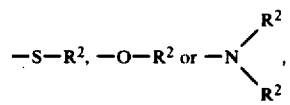

the individual radicals $R^2$ may be identical or different and each is alkyl of 1 to 6 carbon atoms, aralkyl of 7 to 12 carbon atoms or phenyl, the two radicals $R^2$ present as substituents of the nitrogen atom may also form, together with the latter, a 5-membered or 6-membered heterocyclic ring, which in addition to the nitrogen atom may also contain an oxygen atom, each b is a single bond and $R^3$ is amino and $R^4$ is thiocarbamido, or $R^3$ and $R^4$ together are

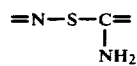

and each b is a double bond. The above radicals and rings may in addition be substituted by groups which are inert under the reaction conditions, e.g. alkyl or alkoxy each of 1 to 4 carbon atoms.

Suitable starting materials II are 2-methyl-, 2-ethyl-, 2-n-propyl-, 2-isopropyl-, 2-n-butyl-, 2-sec.-butyl-, 2-isobutyl-, 2-tert.-butyl, 2-benzyl-, 2-phenyl, 2-o-, 2-m- or 2-p-methylphenyl-, 2-o-, 2-m- or 2-p-methoxyphenyl-, 2-methylmercapto-, 2-ethylmercapto-, 2-n-propylmercapto-, 2-isopropylmercapto-, 2-butylmercapto-, 2-isobutylmercapto-, 2-sec.-butylmercapto-, 2-tert.-butylmercapto-, 2-benzylmercapto-, 2-phenylmercapto-, 2-o-, 2-m- or 2-p-methylphenylmercapto-, 2-o-, 2-m- or 2-p-methoxyphenylmercapto-, 2-methoxy-, 2-ethoxy-, 2-propoxy-, 2-isopropoxy-, 2-butoxy, 2-isobutoxy-, 2-sec.-butoxy-, 2-tert.-butoxy-, 2-benzoxy-, 2-phenoxy-, 2-o-, 2-m- or 2-p-methylphenoxy-, 2-o-, 2-m- or 2-p-methoxyphenoxy-, 2-dimethylamino-, 2-diethylamino-, 2-dipropylamino-, 2-diisopropylamino-, 2-dibutylamino-, 2-diisobutylamino-, 2-di-sec.-butylamino-, 2-di-tert.-butylamino-, 2-dibenzylamino-, 2-diphenylamino-, 2-di-(o-, m- or p-methylphenyl)-amino- and 2-di-(o-, m- or p-methoxyphenyl)-amino-4-amino-5-cyano-thiazole; 2-pyrrolidino-4-amino-5-cyanothiazole, 2-piperidino-4-amino-5-cyano-thiazole and 2-morpholino-4-amino-5-cyano-thiazole; and 4-amino-5-cyano-thiazole.

In general, both steps of the reaction are carried out at from 0 to 150° C., preferably from 15 to 70° C., under atmospheric or superatmospheric pressure, continuously or batchwise. Advantageously, a solvent which is inert under the reaction conditions is used in each step. Examples of suitable solvents are water, dimethylformamide, halohydrocarbons, especially chlorohydrocarbons, e.g. tetrachloroethylene, 1,1,2,2-or 1,1,1,2-tetrachloroethane, amyl chloride, cyclohexyl chloride, dichloropropane, methylene chloride, dichlorobutane, isopropyl bromide, n-propyl bromide, butyl bromide, chloroform, ethyl iodide, propyl iodide, chloronaphthalene, dichloronaphthalene, carbon tetrachloride, 1,1,1-or 1,1,2-trichloroethane, trichloroethylene, pentachloroethane, 1,2-dichloroethane, 1,1-dichloroethane, n-propyl chloride, 1,2-cis-dichloroethylene, n-butyl chloride, 2-, 3- and iso-butyl chloride, chlorobenzene, fluorobenzene, bromobenzene, iodobenzene, o-, p- and m-dichlorobenzene, o-, p- and m-dibromobenzene, o-, m- and p-chlorotoluene, 1,2,4-trichlorobenzene, 1,10-dibromodecane and 1,4-dibromobutane; alkanols and cycloalkanols, e.g. ethanol, methanol, n-butanol, isobutanol, tert.-butanol, glycol, glycerol, n-propanol, isopropanol, amyl alcohol, cyclohexanol, 2-methyl-4-pentanol, ethylene glycol monoethyl ether, 2-ethylhexanol, methylglycol, n-hexanol, isohexyl alcohol, isoheptyl alcohol, n-heptanol, ethylbutanol, nonyl alcohol and dodecyl alcohol; sulfoxides, e.g. dimethyl sulfoxide, diethyl sulfoxide, dimethyl sulfone, diethyl sulfone, methyl ethyl sulfone and tetramethylene sulfone; esters, e.g. methyl acetate, n-propyl acetate, methyl propionate, butyl acetate, ethyl formate, methyl phthalate, methyl benzoate, ethyl acetate and phenyl acetate; nitrohydrocarbons, e.g. nitromethane, nitroethane, nitrobenzene, o-, m- and p-chloronitrobenzene and o-nitrotoluene. In the second step, inorganic or organic acids may also be used, e.g. hydrogen chloride, hydrogen bromide, hydrogen iodide, perchloric acid, sulfuric acid, phosphoric acid, nitric acid, carbon dioxide, sulfonic acids, e.g. benzenesulfonic acid and p-toluenesulfonic acid, aliphatic carboxylic acids, e.g. oxalic acid or formic acid, acetic acid or propionic acid, butyric acid and isobutyric acid, and mixtures of these. Advantageously, the amount of solvent used is from 400 to 10,000 percent by weight, preferably from 500 to 1,000 percent by weight, based on starting material II.

The first step of the reaction is carried out in the presence of a basic compound, advantageously in an amount of from 0.003 to 1 equivalent per mole of starting compound II; preferably, from 0.003 to 0.01 equivalent of basic compound is used in the case of starting materials II which have an aliphatic substituent in the 2-position, and from 0.1 to 1 equivalent of basic compound in the case of all other starting materials II. Preferred basic compounds are alkaline earth metal compounds, alkali metal compounds, ammonium compounds and, especially, tertiary amines, and mixtures of these. However, primary and secondary amines can also be used. Examples of suitable basic compounds are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, sodium formate, sodium acetate, sodium propionate, sodium butyrate, sodium isobutyrate, potassium formate, potassium acetate, potassium propionate, potassium butyrate, potassium isobutyrate, sodium methylate, sodium ethylate, sodium propylate, sodium isopropylate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyltoluidine, N-ethylpyrrolidone, N-methylpiperidine, N-ethylpiperidine, N-methylpyrrolidine, N-ethylpyrrolidine and pyridine, dimethylamine, diethylamine, dipropylamine, diisopropylamine, dibutylamine, diisobutylamine, di-sec.-butylamine, di-tert.-butylamine, dibenzylamine, dicyclohexylamine, diamylamine, dihexylamine, N-methylaniline, N-ethylaniline, N-propylaniline, N-methyltoluidine, N-ethyltoluidine, N-propyltoluidine, N-methylaminoethanol, N-ethylaminoethanol, N-propylaminoethanol, pyrrolidone, piperidine, pyrrolidine, imidazole, pyrrole, methylamine, ethylamine, propylamine, isopropylamine, butylamine, sec.-butylamine, tert.-butylamine, benzylamine, hexylamine, cyclohexylamine, amylamine, aniline, toluidine and ammonia.

In the second step of the process, the starting materials III are reacted with the dehydrogenating agents according to the invention in stoichiometric amount or in excess preferably with from 1 to 3, especially from 1 to 1.5, equivalents of dehydrogenating agent per mole of starting material II. Preferred dehydrogenating agents are phosphorus pentabromide, phosphorus pentachloride, sulfuryl chloride, sulfuryl bromide, chlorine, bromine, iodine, tert.-butyl hypochlorite, tert.-butyl hypobromite, sodium hypochlorite, potassium hypochlorite, sodium hypobromite and potassium hypobromite. An oxidizing agent may also be used as the dehydrogenating agent. The following compounds may be used advantageously: chromium compounds, e.g. potassium bichromate, sodium bichromate, ammonium bichromate, chromic acid and chromyl chloride; permanganates, e.g. potassium permanganate; nitric acid and its salts, e.g. sodium nitrate, silver nitrate, potassium nitrate, lithium nitrate, calcium nitrate, magnesium nitrate, nickel nitrate, chromium nitrate, copper nitrate, cobalt nitrate, cerium nitrate, thorium nitrate, bismuth nitrate, iron nitrate and mercury nitrate; sulfuric acid; metal oxides, e.g. PbO, $PbO_2$, CuO, $OsO_4$, $RuO_4$, HgO, $SeO_2$ and $Ag_2O$; metal salts, e.g. iron-III chloride, iron-III cyanides such as potassium ferricyanide, copper salts, e.g. the chlorides, sulfates and acetates, lead tetraacetate, manganese tetraacetate, mercury-I acetate, mercury-II acetate and silver chlorate; organic oxidizing agents, e.g. chloranil and potassium nitrosodisulfonate; and ozone. Further advantageous oxidizing agents are oxygen and mixtures containing oxygen, e.g. air, used by themselves or, advantageously, in the presence of catalysts, e.g. oxides of iron, chromium, aluminum, copper, lead, cobalt, molybdenum, vanadium, tungsten or zinc, with or without alkali metal oxides, and mixtures of the above; bromine and bromides; nickel, cobalt, copper, manganese, lead, cerium, mercury and barium salts, e.g. the corresponding acetates, sulfates and chlorides; aluminum chloride; molybdates, e.g. the molybdates of copper, uranium, tin, boron, iron and chromium, and nickel, platinum, palladium, osmium, rhodium, iridium, ruthenium, silver and zinc. Where oxygen is used as the oxidizing agent, it is advantageously used in the proportion of from 0.05 to 2 moles per mole of starting material II. In a further preferred embodiment, hydrogen peroxide is used as the oxidizing agent, and is advantageously employed in the form of an aqueous solution of from 5 to 60 percent strength by weight, preferably from 10 to 50 percent strength by weight. Under certain circumstances, compounds which form hydrogen peroxide under the reaction conditions may also be used, for example inorganic or organic peroxy compounds, e.g. sodium peroxide, potassium peroxide, magnesium peroxide, calcium peroxide, zinc peroxide, barium peroxide, hydroperoxides, e.g. $NaOOH.0.5\ H_2O_2$ and $NH_4OOH$, corresponding hydrates, e.g. $CaO_2.8H_2O$, peroxy-hydrates, e.g. $BaO_2.H_2O_2$ and $BaO_2.2H_2O_2$, peroxycarbonates, e.g. sodium peroxycarbonate and calcium peroxycarbonate, and peroxyphosphates, e.g. potassium peroxydiphosphate.

In a further preferred embodiment, sulfuric acid of from 86 to 110 percent strength by weight is used as the dehydrogenating agent, at from 60° to 120° C. Advantageously, the sulfuric acid is used in combination with the above oxidizing agents, especially with halogens, halides and acid chlorides. Suitable amounts are from 3 to 10 moles, preferably from 5 to 7 moles, of sulfuric acid with or without from 0.01 to 0.15, preferably from 0.5 to 0.1, equivalent of oxidizing agent per mole of starting material II. If both sulfuric acid and an oxidizing agent are used, a temperature of from 20° to 80° C. is particularly preferred.

The reaction may be carried out as follows: a mixture of starting material II, basic compound and hydrogen sulfide, with or without solvent, is kept at the reaction temperature for from 0.5 to 24 hours. The compound III is isolated from the reaction mixture in the conventional manner, e.g. by filtration, if necessary after precipitation. To carry out the second step, it is advantageous to dissolve or suspend compound III in the solvent used and then to add a dehydrogenating agent or oxidizing agent whilst stirring. Advantageously, the starting mixture is first cooled, and when the initially exothermic reaction has subsided, the mixture is briefly heated, for example for from 10 to 60 minutes. If is also possible to add the dehydrogenating agent to the reaction mixture from the first step, without isolating compound III, with or without first removing the solvent from the first step and/or adding the solvent for the second step, and thus to carry out the second step, i.e. the cyclization.

The second reaction step can be carried out as follows: a mixture of compound III, dehydrogenating agent and, in most cases, a solvent is kept at the reaction temperature for from 0.5 to 3 hours. More particularly, it is advantageous to dissolve or suspend compound III in the solvent used and then to add the oxidizing agent whilst stirring. It is advantageous to cool the starting mixture initially and to heat it briefly, for example for from 0.5 to 60 minutes, after the initially exothermic reaction has subsided. The end product is then isolated from the reaction mixture in the conventional manner, for example by filtration, if necessary after precipitation from a solution in a solvent. As a rule, the salts of the end products I are isolated; the free amines are advantageously obtained from the salts by dissolving or suspending the latter in water or in one of the above organic solvents and treating them with bases, for example one of the above bases, preferably sodium hydroxide solution, potassium hydroxide solution, ammonia, sodium carbonate, potassium carbonate, pyridine or triethylamine.

The new 3-amino-thiazolo-(4,5-c)-isothiazoles I, 4-amino-5-thiocarbamidothiazoles III and 4,5-disubstituted thiazoles IV, which may be obtained by the process of the invention, are valuable intermediates for the preparation of azo dyes and crop protection agents. For example, if 3-amino-5-methylmercaptothiazolo-(4,5-c)-isothiazole in a mixture of sulfuric acid and glacial acetic acid, is diazotized with nitrosylsulfuric acid, a diazonium salt solution is obtained, which couples with aniline derivatives to give azo dyes ranging from red to violet. These dyes may be used to dye polyester fibers and nylon fibers in brilliant hues with good fastness properties, especially with very good wetfastness.

The parts referred to in the Examples are by weight and bear the same relation to parts by volume as that of the kilogram to the liter.

EXAMPLE 1

(a)

2-Methylmercapto-4-amino-5-thiocarbamoylthiazole 20 parts of hydrogen sulfide are introduced, over 6 hours, into a mixture of 51.3 parts of 2-methylmercapto-4-amino-5-cyanothiazole, 0.2 part of triethylamine and 150 parts of dimethylformamide. The reaction mixture is left to stand for 48 hours and is then poured into 500 parts of ice water, and the product is filtered off. 33 parts of 2-methylmercapto-4-amino-5-thiocarbamoyl-thiazole (54% of theory) of melting point 192°–195° C. are obtained.

(b)

3-Amino-5-methylmercapto-thiazolo-(4,5-c)-isothiazole 15 parts of 2-methylmercapto-4-amino-5-thiocarbamoylthiazole are introduced, at 30° C., into 100 parts of sulfuric acid (of 98 percent strength by weight), containing 0.5 part of bromine. When the evolution of gas has subsided (after 10 minutes), the mixture is stirred for 10 minutes at 45° C. and is then poured on to 300 parts of ice, the batch is filtered and the filter residue is stirred with 100 parts of aqueous 30 percent by weight ammonia solution and filtered off. 12.5 parts of 3-amino-5-methylmercapto-thiazolo-(4,5-c)-isothiazole (84% of theory) of melting point 160°–166° C. are obtained.

EXAMPLE 2

(a) 2-Ethylmercapto-4-amino-5-thiocarbamoylthiazole 55.5 parts of 2-ethylmercapto-4-amino-5-cyano-thiazole are reacted with 20 parts of hydrogen sulfide as described in Example 1(a). 32.1 parts of 2-ethylmercapto-4-amino-5-thiocarbamoylthiazole (49% of theory) of melting point 180°–183° C. are obtained.

(b)

3-Amino-5-ethylmercapto-thiazole-(4,5-c)-isothiazole 27.1 parts of 2-ethylmercapto-4-amino-5-thiocarbamoylthiazole are reacted with 270 parts of sulfuric acid and 0.5 part of bromine as described in Example 1(b). 23.4 parts of 3-amino-5-ethylmercapto-thiazolo-(4,5-c)-isothiazole (87% of theory) of melting point 131°–134° C. are obtained.

EXAMPLE 3

(a) 2-Pyrrolidino-4-amino-5-cyano-thiazole 40 parts of 2-methylmercapto-4-amino-5-cyano-thiazole are dissolved in 200 parts of dimethylsulfoxide and 45 parts of pyrrolidine are added. The mixture is heated for 6 hours at 60° C. and the product is filtered off. 41.5 parts of 2-pyrrolidino-4-amino-5-cyano-thiazole (91% of theory) of melting point 305°–308° C. are obtained.

(b) 2-Pyrrolidino-4-amino-5-thiocarbamoyl-thiazole 25 parts of 2-pyrrolidino-4-amino-5-cyanothiazole are reacted with 8 parts of hydrogen sulfide in 150 parts of dimethylformamide and 2 parts of triethylamine, by the method described in Example 1(a). 15.6 parts of 2-pyrrolidino-4-amino-5-thiocarbamoyl-thiazole (53% of theory) of melting point 264°–265° C. are obtained.

(c) 3-Amino-5-pyrrolidino-thiazolo-(4,5-c)-isothiazole 11 parts of 2-pyrrolidino-4-amino-5-thiocarbamoyl-thiazole in 70 parts of sulfuric acid are oxidized with 0.5 part of bromine by the method described in Example 1(b). 10 parts of 3-amino-5-pyrrolidino-thiazolo-(4,5-c)-isothiazole (91% of theory) of melting point 270°–273° C. are obtained.

EXAMPLE 4

3-Amino-5-pyrrolidino-thiazolo-(4,5-c)-isothiazole 5 parts of 2-pyrrolidino-4-amino-5-thiocarbamoyl-thiazole prepared as described in Example 3(a) and 3(b) are suspended in 50 parts of glacial acetic acid and 1 part of 50 percent strength by weight hydrogen peroxide is added at 20° C. Thereupon, the temperature rises to 30° C. After stirring for one hour at 22° C., the end product is precipitated by means of 100 parts of water, and is filtered off. 4.1 parts (82% of theory) of melting point 262°–264° C. are obtained.

EXAMPLE 5

(a) 2-Phenyl-4-amino-5-cyano-thiazole 21 parts of cyanamide and 83 parts of ethyl thiobenzoate are successively introduced into a solution of 12.5 parts of sodium in 260 parts of ethanol, and the mixture is refluxed for one hour at 78° C. It is then left to stand for 12 hours, 40 parts of chloroacetonitrile are added, and the reaction mixture is refluxed for one hour at 78°

C. The product is precipitated by means of 300 parts of water, and filtered off. 78 parts of 2-phenyl-4-amino-5-cyano-thiazole (78% of theory) of melting point 178°–179° C. are obtained.

(b) 2-Phenyl-4-amino-5-thicarbamoylthiazole 75 parts of 2-phenyl-4-amino-5-cyanothiazole in 300 parts of dimethylformamide and 15 parts of triethylamine are reacted with 13 parts of hydrogen sulfide as described in Example 1(a). 77 parts of 2-phenyl-4-amino-5-thiocarbamoylthiazole (89% of theory) of melting point 164°–167° C. are obtained.

(c) 3-Amino-5-phenyl-thiazolo-(4,5-c)-isothiazole 7 parts of 30 percent strength by weight hydrogen peroxide are added to 12.8 parts of 2-phenyl-4-amino-5-thiocarbamoylthiazole in 150 parts of methanol. The mixture is stirred for 12 hours at 22° C. and the product is then filtered off. 7.9 parts of 3-amino-5-phenyl-thiazolo-(4,5-c)-isothiazole (62% of theory) of melting point 176°–179° C. are obtained.

EXAMPLE 6

(a) 2-Methyl-4-amino-5-thiocarbamoylthiazole 5.5 parts of 2-methyl-4-amino-5-cyano-thiazole in 50 parts of dimethylformamide and 10 parts of triethylamine are reacted with 3 parts of hydrogen sulfide as described in Example 1(a). 4.0 parts of 2-methyl-4-amino-5-thiocarbamoylthiazole (58% of theory) of melting point 209°–213° C. are obtained.

(b) 3-Amino-5-methyl-thiazolo-(4,5-c)-isothiazole 3.4 parts of 2-methyl-4-amino-5-thiocarbamoylthiazole are suspended in 50 parts of glacial acetic acid and one part of 30 percent strength by weight hydrogen peroxide is added. After stirring for 12 hours at 22° C., the product is filtered off. 1.7 parts of 3-amino-5-methyl-thiazolo-(4,5-c)-isothiazole (50% of theory) of melting point 164°–167° C. are obtained.

We claim:

1. A process for the manufacture of a 3-amino-thiazolo-(4,5-c)-isothiazole of the formula

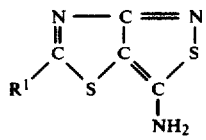

where $R^1$ is hydrogen, alkyl of 1 to 6 carbon atoms, aralkyl of 7 to 12 carbon atoms, phenyl,

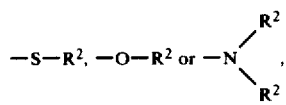

the individual radicals $R^2$ are identical or different and each is alkyl of 1 to 6 carbon atoms, aralkyl of 7 to 12 carbon atoms or phenyl, the two radicals $R^2$ present as substituents of the nitrogen atom may also form, together with the latter, a 5-membered or 6-membered heterocyclic ring, which in addition to the nitrogen atom may also contain an oxygen atom, wherein the above radicals and rings may in addition be substituted by alkyl or alkoxy each of 1 to 4 carbon atoms, which process comprises: in a first step, reacting a 4-amino-5-cyanothiazole of the formula

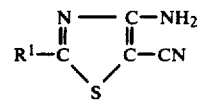

where $R^1$ has the above meaning, with hydrogen sulfide in the presence of at least one basic compound selected from the group consisting of alkaline earth metal compounds, alkali metal compounds, ammonium compounds, tertiary amines, primary amines or secondary amines, and, in a second stage, cyclizing the resulting 4-amino-5-thiocarbamido-thiazole of the formula

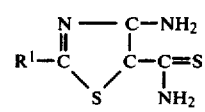

where $R^1$ has the above meaning, in the presence of a dehydrogenating agent.

2. A process as set forth in claim 1, wherein the first step of the reaction is carried out with from 1 to 3 moles of hydrogen sulfide per mole of starting material II.

3. A process as set forth in claim 1, wherein the first step of the reaction is carried out with sodium sulfide, potassium sulfide, ammonium bisulfide, sodium bisulfide or potassium bisulfide.

4. A process as set forth in claim 1, wherein both steps of the reaction are carried out at from 0° to 150° C.

5. A process as set forth in claim 1, wherein both steps of the reaction are carried out at from 15° to 70° C.

6. A process as set forth in claim 1, wherein both steps of the reaction are carried out in the presence of solvents which are inert under the reaction conditions and are used in an amount of from 400 to 10,000 percent by weight, based on starting material II.

7. A process as set forth in claim 1, wherein the first step of the reaction is carried out in the presence of a basic compound used in an amount of from 0.003 to 1 equivalent per mole of starting material II.

8. A process as set forth in claim 1, wherein the second step of the reaction is carried out with from 1 to 3 equivalents of dehydrogenating agent per mole of starting material II.

9. A process as set forth in claim 1, wherein the second step of the reaction is carried out with phosphorus pentabromide, phosphorus pentachloride, sulfuryl chloride, sulfuryl bromide, chlorine, bromine, iodine, tert.-butyl hypochlorite, tert.-butyl hypobromite, sodium hypochlorite, potassium hypochlorite, sodium hypobromite or potassium hypobromite.

10. A process as set forth in claim 1, wherein the second step of the reaction is carried out with oxygen as the oxidizing agent, used in a ratio of from 0.05 to 2 moles per mole of starting material II.

11. A process as set forth in claim 1, wherein the second step of the reaction is carried out with hydrogen peroxide.

12. A process as set forth in claim 1, wherein the second step of the reaction is carried out with sulfuric acid in combination with halogens, halides or acid chlorides.

* * * * *